US005590657A

United States Patent [19]
Cain et al.

[11] Patent Number: 5,590,657
[45] Date of Patent: Jan. 7, 1997

[54] PHASED ARRAY ULTRASOUND SYSTEM AND METHOD FOR CARDIAC ABLATION

[75] Inventors: Charles A. Cain; Emad S. Ebbini; S. Adam Strickberger, all of Ann Arbor, Mich.

[73] Assignee: The Regents of The University of Michigan, Ann Arbor, Mich.

[21] Appl. No.: 554,134

[22] Filed: Nov. 6, 1995

[51] Int. Cl.$^6$ .................................................. A61B 8/00
[52] U.S. Cl. ................................. 128/660.03; 128/662.06; 601/3
[58] Field of Search .................. 606/27, 28; 607/97, 607/122; 601/2–4; 128/660.03, 662.06

[56] References Cited

U.S. PATENT DOCUMENTS

| | | | |
|---|---|---|---|
| 4,852,577 | 8/1989 | Smith et al. | 128/660.07 |
| 4,938,217 | 7/1990 | Lele | 601/3 X |
| 4,977,902 | 12/1990 | Sekino et al. | 601/3 X |
| 5,172,343 | 12/1992 | O'Donnell | 367/7 |
| 5,222,501 | 6/1993 | Ideber et al. | 128/662.06 X |
| 5,263,493 | 11/1993 | Avitall | 607/122 |
| 5,295,484 | 3/1994 | Marcus et al. | 128/660.03 |
| 5,381,792 | 1/1995 | Yanagida et al. | 128/660.03 |
| 5,487,306 | 1/1996 | Fortes | 128/661.01 X |
| 5,524,620 | 6/1996 | Rosenschein | 601/2 X |

OTHER PUBLICATIONS

Phased Aberration Correction and Motion Compensation for Ultrasonic Hyperthermia Phased Arrays: Experimental Results—Wang, Ebbinin, O'Donnell, Cain, Jan. 1994—IEEE Transactions on Ultrasonics, Ferroelectrics, and Frequency Control, vol. 41, No. 1.

*Primary Examiner*—Francis Jaworski
*Attorney, Agent, or Firm*—Harness, Dickey & Pierce, PLC

[57] ABSTRACT

An ultrasound system and method for performing relatively non-invasive cardiac ablation on a patient. The system of the present invention includes a plurality of ultrasound transducers forming a phased array that is to be located externally of the patient. The array a focused beam of sufficient energy to ablate a predetermined cardiac tissue volume. The system is capable of refocusing the beam so that acoustical aberrations encountered by the beam, as it is transmitted through inhomogeneous body tissues between the array and the treatment volume, are taken into account and will not impede operation of the system. To refocus the beam, the system includes a senor which senses the phase distribution caused by the aberrations allowing a controller to calculate a compensating driving phase distribution and accordingly drive the array. The system also allows for real time correction of the beam's position enabling the beam to follow a moving myocardial target volume.

39 Claims, 6 Drawing Sheets

PHASED ARRAY ULTRASOUND SYSTEM AND METHOD FOR CARDIAC ABLATION

BACKGROUND OF THE INVENTION

1. Field of the Invention

The present invention generally relates to the performance of cardiac ablation in order to eliminate abnormal heart rhythms or arrhythmia. More specifically, the present invention relates to a relatively non-invasive, phased array ultrasound cardiac ablation system and method which is capable of compensating for acoustic aberrations between the array and the cardiac tissue. The system also compensates for movement of the treatment volume during the ablation procedure.

2. Description of the Prior Art

Currently, a variety of treatments are available for abnormal heart rhythms, hereinafter arrhythmias, such as atrial fibrillation, supraventricular arrhythmias, ventricular fibrillation, ventricular tachycardia, bradycardia and others. These treatments include both surgical and non-surgical treatments. The non-surgical treatments are principally through the use of anti-arrhythmic drugs while the surgical treatments involve implantable devices and ablation of cardiac tissue.

Anti-arrhythmic drugs slow the intercardiac impulses which sustain the arrhythmia once started. These drugs decrease the likelihood that an arrhythmia will occur. Atrial fibrillation, the most common arrhythmia, is often treated in this manner. As well documented in the literature, currently available anti-arrhythmic drugs exhibit undesirable side effects and can prove fatal in extreme cases. For this reason, surgical alternatives are often used and preferred.

Until recently, implantable cardiac defibrillators have been the surgical treatment of choice for life threatening arrhythmias. An automatic, implantable cardioverter defibrillator (ICD), is used to shock the heart and stop an ongoing arrhythmia. After the shock, normal sinus rhythm resumes. ICDs have become an accepted treatment for ventricular arrhythmias. These arrhythmias generally do not respond to drug treatments. Another device, "Pacemakers", as they are generally known, are programmable implantable units that stimulate and control excessively slow cardiac rhythms through a series of electrical impulses.

Both pacemakers and ICDs respond to the electrophysical basis of ventricular arrhythmias. Neither, however, corrects the root cause of the arrhythmia and for this reason is possible for the arrhythmia to recur. The ICD functions by discharging a high voltage capacitor which is conductively connected to the heart. The energy required for successive discharges requires that the device's battery be periodically replaced. The implantation of both of the above devices requires surgery and, with the ICD, the total cost of the device and the implantation is in the $50,000 dollar range. In addition to its high cost, with an ICD, a constant expectation of an unpleasant "shock" sensation remains with some patients. To some, this poses a significant psychological burden.

Another surgical treatment for arrhythmia, tissue ablation, actually corrects the underlying electrophysiological cause of the arrhythmia. Tissue ablation generally involves the transmission of energy to a selected portion of cardiac tissue to ablate the tissue. In some situations, tissue ablation is utilized as an adjunct therapy for patients with implantable defibrillators. Some arrhythmias, however, are not amenable to ablation because of limitations in the techniques currently being used. One example is ventricular tachycardia.

Current developmental ablation techniques use a variety of energy sources including direct current (DC) energy; radio frequency (RF) energy; microwave energy; cryothermic energy; and laser energy.

In direct current, myocardial tissue ablation, a common catheter is inserted into the heart and 2,000 to 4,000 volts of electricity are applied over several milliseconds. Ablation according to this technique is performed under general anesthesia due to the severity of the muscular contractions associated with the electrical shock used during the procedure. Damage to the catheters used in delivering these high voltages has been seen and, as a result, the generation of an electrical discharge at a non-intended site within the patient is possible.

RF ablation of myocardial tissue is similar in that it is a catheter based technique which induces tissue damage to eliminate the arrhythmia. With RF ablation, 40 to 60 volts of energy are used to thermally treat the desired tissue. One significant limitation on the use of RF ablation techniques is that the low energy generation and the significant dissipation of this energy after delivery result in the size of the ablated area being very limited. The treatment is also limited to those areas which can be reached by a catheter based RF probe.

Having all the general limitations associated with RF ablation techniques, microwave ablation techniques are similarly limited. Additionally, microwave energy tends to be difficult to focus. This is because of the relatively long wavelengths of the frequencies believed necessary for ablation.

Catheters having cyroprobes on their end have also used to ablate cardiac tissue. Perforation of the cardiac tissue is a danger with this method since the temperatures required to adequately perform ablation (−78° C.) require that a large catheter tip is used.

Laser ablation techniques seem to hold some promise, but some concerns remain regarding tissue perforation, equipment deterioration, equipment durability and portability.

With all of the above described systems, ablation is discussed as being performed through a fully invasive method. In each system, the source of the energy required for performing ablation is applied via a catheter which is inserted into the patient to the appropriate treatment area through a venous or arterial route. The procedures are also tedious and do not always allow for the catheter to be placed as close as necessary to the tissue in need of treatment. Non-invasive systems are an attractive alternative.

Catheter based ultrasonic transducers have also been proposed for ablating cardiac tissue. Although not available commercially, single and phased array transducers have been suggested in the relevant literature. An electrode also associated with the distal end of the catheter is used to electrically map the conduction pattern in the heart. The electrode aids in positioning and orienting a transducer relative to the target tissue. The transducers typically generate frequencies in the 1–40 Mhz range.

Like the other energy based ablation techniques mentioned above, the catheter based ultrasound technique is an invasive procedure. Additionally, manufacturing a phased array transducer of a size capable of being mounted to the end of a catheter, is currently not practical because of the number of transducers involved and because of the necessary size of the array required for adequate ablation.

In designing a relatively or completely non-invasive system, one where the source of the ablation energy is external of the patient, requires that aberrations created by tissues in the treatment "window" overlying the heart must be considered. Movement of the heart itself must also be considered when delivering energy from an external source.

If the above are overcome, relatively or wholly non-invasive procedures have the potential of increasing overall quality of the treatment as well as increasing the number of patients that can be treated and reducing cost. Cost savings would be realized not only from the surgical techniques themselves, but also by decreasing patients being treated with implantable defibrillators and by "curing" patients already having implants, as opposed to merely arresting an occurring arrhythmia.

In view of the foregoing limitations and shortcomings of the prior art devices, as well as other disadvantages not specifically mentioned above, it should be apparent that there still exists a need in the art for a relatively or wholly non-invasive cardiac ablation system and method.

It is therefore a primary object of this invention to fulfill that need by providing a cardiac ablation system and method which operates in a relatively or wholly non-invasive manner.

Another object of this invention is to provide a cardiac ablation system and method which can perform the ablation procedure as a wholly non-invasive procedure.

Still another object of this invention is to provide an apparatus and method whereby cardiac ablation is available to treat atrial fibrillation, supraventricular arrhythmias, ventricular fibrillation, ventricular tachycardia and bradycardia.

It is also an object of the present invention to provide a cardiac ablation system and method which is capable of focusing on a specific cardiac tissue treatment volume.

A further object of this invention is to provide a cardiac ablation system and method which can correct for significant aberrations in the treatment window between the energy emitter and the heart of the patient.

Still another object of this invention is to provide an apparatus and method for cardiac ablation where movement of the treatment volume is compensated for during the performance of ablation.

A further object of this invention is to provide an apparatus and method for cardiac ablation which is capable of making large lesions and ablating relatively large treatment volumes.

Still another object of this invention is to provide a system and method for performing cardiac ablation while using ultrasonic energy.

Another object of this invention is to provide an apparatus and method for cardiac ablation which utilizes a phased ultrasound array located externally of the patient.

SUMMARY OF THE INVENTION

Briefly described, these and other objects are accomplished according to the present invention by providing an ultrasound system for performing relatively non-invasive cardiac ablation on a patient. The ultrasound system of the present invention generally includes a plurality of ultrasound transducers formed into an array which is intended to be externally located relative to the patient. The ultrasound transducers produce ultrasonic energy in the form of a focused beam having sufficient energy to ablate a predetermined cardiac tissue volume of the patient's heart. The array is electrically coupled to a microprocessor based controller and to drivers. The controller produces electrical control signals which are communicated through the amplifier and matching circuits of the drivers to produce an electrical current that is applied to the transducers of the array. As a result, an appropriately phased ultrasound wave is produced by each transducer and the waves combine to form an ultrasound beam that is focused on the appropriate cardiac tissue volume.

The system is additionally able to refocus the beam in order to compensate for significant acoustical aberrations encountered by the beam as it is transmitted through inhomogeneous body tissues located between the array and the treatment volume. To refocus the beam, the system includes a sensor which senses the phase distribution which results from the aberrations. This information is communicated via feedback signals back to the controller where a compensating driving phase distribution is calculated. The compensating phase distribution is communicated via compensating control signals to the drivers and the drivers cause the transducers to produce a phased compensated ultrasound beam which refocuses on the treatment volume and performs cardiac ablation.

In addition to the focus correction capabilities of the present system, the present invention also allows for the real time correction of the beam's position relative to the treatment volume. This enables the beam to follow a moving myocardial target volume. Such movement can be a result of the cardiac cycle itself or movement of the patient. Generally, a sensing element monitors the movement of the myocardial target volume and senses the position of the ultrasound beam relative to the now moved treatment volume. This information is then transferred via feedback signals to the controller which calculates and determines a compensated movement phase distribution. The compensated movement phase distribution is then communicated to the drivers which in turn cause the ultrasound beam to be refocused on the new position of the myocardial target volume. Since electronic control is being utilized to refocus the beam at the new position, reformation of the beam is sufficiently fast enough to allow the tracking of the myocardial treatment volume within the cardiac cycle.

Additional benefits and advantages of the present invention will become apparent to those skilled in the art to which the present invention relates from the subsequent description of the preferred embodiment and the appended claims, taken in conjunction with the accompanying drawings.

DETAILED DESCRIPTION OF THE PREFERRED EMBODIMENT

Figure 1:
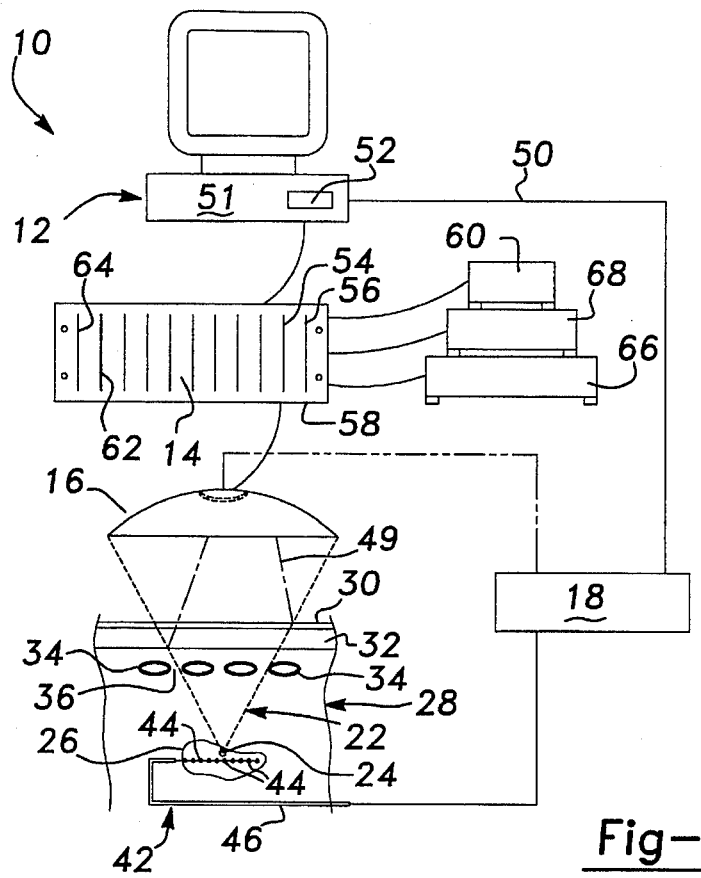
FIG. 1 is a schematic illustration of an apparatus embodying the principles of the present invention.

Referring now to the drawings, the system used for performing myocardial tissue ablation according to the method of the present invention is generally illustrated in FIG. 1 and designated at 10. The system generally includes a microprocessor based controller 12, a network of drivers 14, an ultrasound array 16 and a phase detection subsystem 18, which can be of several varieties.

The array 16 is a specialized source of ultrasound energy and is based on multiple ultrasound transducers 20 (see FIG. 2) arranged in a two dimensional array such that each transducer 20 is driven separately by the drivers 14. Experimental studies of the present inventors have shown that through use of the controller 12, drivers 14 and phase detection subsystem 18, the phase of the ultrasound waves produced by each transducer 20 can be adjusted to form a highly focused ultrasound beam, generally designated at 22, which can be formed on a predetermined portion of myocardial tissue (the treatment volume 24) on the heart 26 of the patient 28. These studies have also shown that through the present system 10, the beam 22 can also be adjusted to compensate for acoustic aberrations encountered during transmission through the treatment window in the patient 28 and can be adjusted to follow movement of the treatment volume 24 during the cardiac cycle or movement of the patient 28. The focused position of the beam 22 is therefore determined by the phase distribution of all of the transducers 20 of the array 16, hence the term "phased array".

Figure 2:
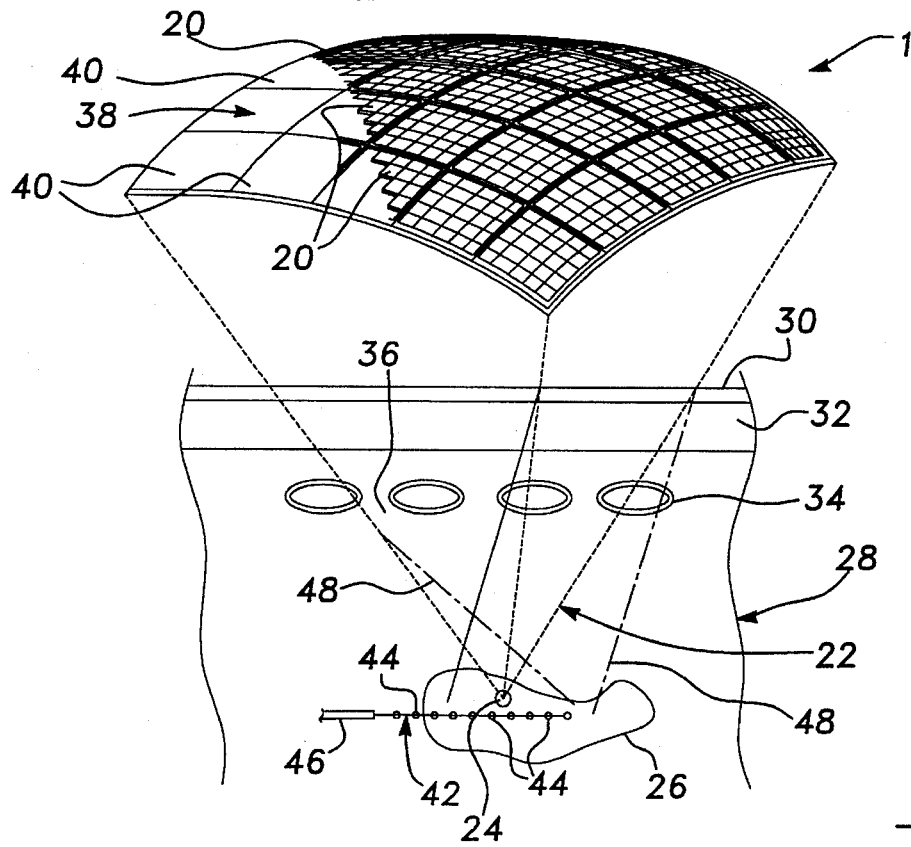
FIG. 2 is an enlarged schematic illustration of the phased array utilized with the present invention.
Figure 3:
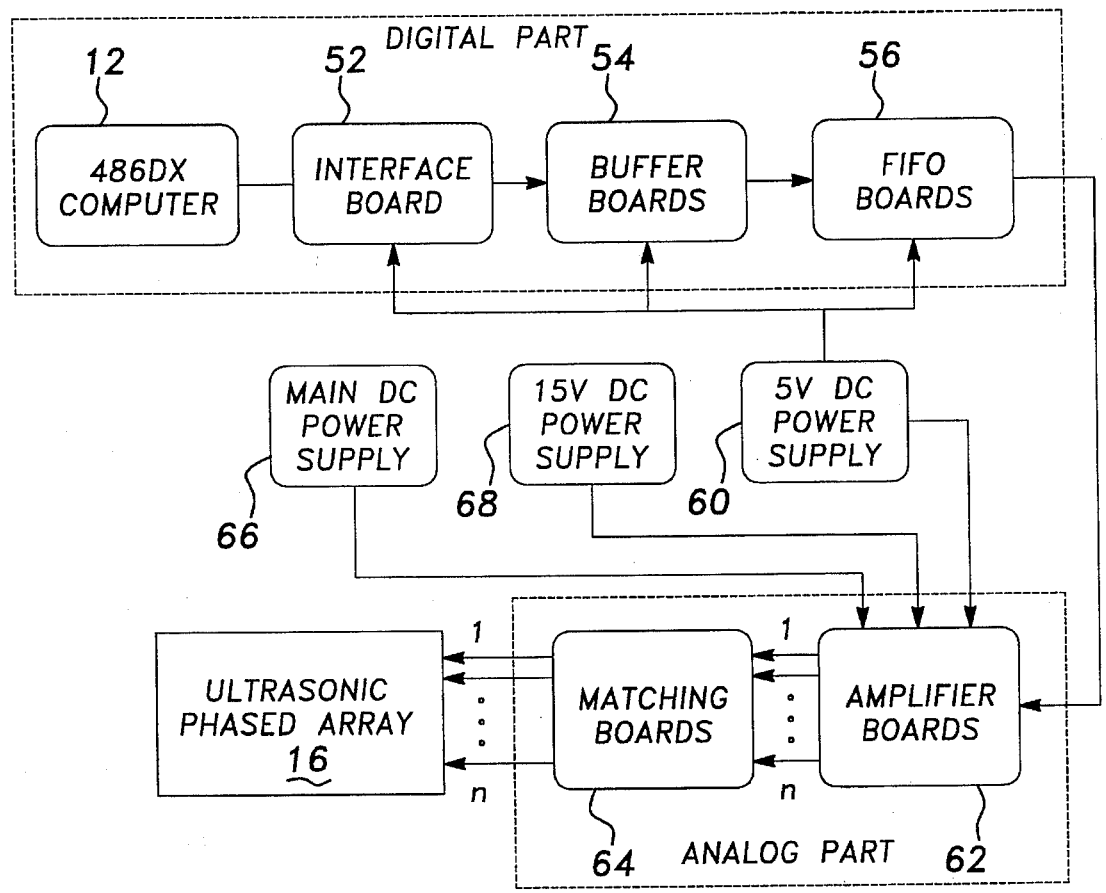
FIG. 3 is a schematic diagram of portions of the electrical components utilized in the present invention.

The array 16 consists of numerous small individual ultrasonic transducers 20 and is designed so that its shape will fit a particular "window" into the treatment volume 24 of interest inside the body of the patient 28. Depending on the particular application, the geometry of overall array 16 can therefore vary greatly. Where the treatment volume 24 consists of a myocardial target, the window consists of that part of the body surface where ultrasound propagation from the array 16 to the target volume 24 will occur. As seen in FIGS. 1 and 2, the window may include a complex set of contiguous, non-contiguous and inhomogeneous tissues such as those formed by skin tissue 30, muscle tissue 32, bone tissue (herein illustrated as and referred to ribs) 34 and the intercostal spaces 36 between the ribs 34. Because of the inhomogeneous nature of the various tissues, the individual ultrasonic waves produced by the transducers 20 are caused to defract, refract and reflect when transmitted therethrough. This results in an unfocused or distorted beam generally designated by the dashed-dot lines at 48 in FIG. 2. In addition to the distorted beam which is transmitted, additional waves are scattered and reflected back toward the array 16. This is representatively designated at 49 in FIG. 1.

The number of transducers 20 in the array 16 can vary, preferably from 30 to greater than 1000, and each is separately driven. As further described herein, the phased array 16 includes 512 individual transducers 20.

The individual ultrasound transducers 20 of the array 16 are small enough to allow a broad dispersion of ultrasound energy coming usually from a fraction of an acoustic wavelength at the operation frequency (preferably from 0.5–2.0 Mhz) to three or four wavelengths. The individual transducers 20 are constructed of a piezoelectric material in the form of blocks or tiles which are bonded to the back of a substrate 38. In the illustrated embodiment of FIG. 2, the transducers 20 have a monolithic, flat rectangular shape and are individually bonded to the substrate 38.

The substrate 38 can be constructed from a variety of materials, including ceramics or metallic materials, such as aluminum or magnesium, and is formed in the desired geometric shape of the array 16. As seen in FIG. 2, the substrate 38 is formed with a plurality of flat mounting areas 40 which are oriented relative to one another so as to provide the array 16 with a generally curved configuration that geometrically provides a degree of focusing to the array 16. In addition to providing a mounting for the transducers 20, the substrate 38 can also serve as a waterproof mounting and as an acoustic impedance matching layer. If constructed of metal, the substrate 38 can additionally act as the common ground electrode for all of the transducers 20.

Alternative fabrication methods than those discussed above can be used to construct the array 16. One illustrative example is that a piezoelectric composite can be molded into the desired final geometry of the array 16 so as to form a continuously curving surface. In addition to the electronic phased focusing of the array, this type of array typically has additional focusing built into its construction as a result of the geometric shape of the array itself. As mentioned above, the shape of the array 16 can also be varied based on design considerations relating to obtaining a good fit with the treatment window into the treatment volume 24.

Since phased arrays 16 and their construction are generally known within the industry, one skilled in this technology will appreciate the various possible choices of construction materials and methods for an array 16 used in a particular application and further in accordance with the teachings of the present invention as described elsewhere herein. For this reason, additional details relating to the construction of the array 16 are not discussed herein.

In order for the system 10 of the present invention to perform cardiac ablation on the treatment volume 24, the system 10 must be able to correct for the acoustic aberrations mentioned above, as well as the movement of the heart 26 and tissue present between array 16 and the treatment volume 24. If the phase relationship between the ultrasound wave from each element transducer 20 and a point in the treatment volume is measured and known, the beam can be refocused by compensating for the presence of the aberrations. Since movement can be considered as a form of aberration, the beam 22 can be periodically refocused as the treatment volume 24 moves thus allowing the focused beam 22 to follow the motion of the treatment volume 24. Obviously, the movement correction of the beam 22 has to be sufficiently fast to allow the beam to accurately follow the treatment volume 24. The hardware and signal processing algorithms which allow for the refocusing of the beam 22 and tracking of the cardiac treatment volume 24 will now be described in greater detail.

By knowing the location of the treatment volume 24 within the heart 26 and the distance of the treatment volume 24 from the array 16, the phase of each transducer 20 is adjusted so that the array 16 focuses the ultrasound beam 22 on the treatment volume 24. In order to locate the treatment volume 24, the phase detection subsystem 18 includes a catheter based sensor array 42 is inserted into the heart 26 by either an arterial or venous route. Such sensor arrays 42 are well known in the industry and includes a number of sensors or hydrophones 44 located along a length of a catheter 46. A separate set of electrodes are initially used to electrically map the conduction pattern in the heart 26 by well known and established procedures. In this manner, the specific location of the myocardia tissue creating the arrhythmia and in need of treatment is identified and located. Using this information, which is fed back into the controller 12 through line 50, the beam 22 can be initially focused on the treatment volume 24.

Also, non-invasive ultrasound imaging techniques which sense temperature increases can be used to initially locate the beam 22 on the treatment volume.

During transmission through the treatment window into the patient 28, the individual ultrasound waves generated by the array 16 will be refracted and reflected as a result of the tissues 30, 32 and 34 and intercostal spaces 36. The result is the defocused beam 48 which is sufficiently defocused so as to preclude ablation of the treatment volume 24.

Utilizing appropriate hydrophones 44 in the sensor array 42 and knowing the distance from the sensor array 42 to the individual transducers 20 of the array 16, it is possible to measure the aberrated phased distribution 24 of the beam 48 after encountering the inhomogeneous tissues of the window into the treatment volume 24.

The distorted phase distribution (or phase error distribution) caused by the aberrations within the window into the treatment volume 24 is communicated through line 50 to the controller 12. Utilizing this information, the controller 12 calculates a compensating driving phase distribution which results in the formation of the focused beam 22 on the treatment volume 24. Known methods for calculating the compensated driving phase distribution are utilized and therefore only generally described below. After refocusing, the intensity of the beam 22 on the treatment volume 24 will be such that ablation of the treatment volume 24 can be performed.

As a completely non-invasive alternative to the above method for determining the effect of the aberrations, appropriate sensors 49 can be positioned within the array 16 itself and used to measure the scattered or reflected phase distribution of the ultrasound waves. Alternatively, the array itself could be used as the appropriate sensors by incorporating receive circuitry into the design. This information is in turn communicated to the controller 12 where a compensating phase distribution is calculated and determined in similar fashion using known non-invasive aberration correction methods.

Movement of the treatment volume 24, as a result of the cardiac cycle or movement of the patient 28, is compensated for by correcting the focus of the beam 22 such that it follows the movement of the treatment volume. This is again achieved through the hydrophone array 42 and is more specifically accomplished by using the array 42 to measure the movement of treatment volume 24 relative to the location of the focused beam 22. Signals corresponding to the relative change in position of beam 22 are then communicated to the controller 12 which accordingly adjusts the phase distribution of the transducers 20 in the array 16 to cause movement of the focused beam 22 to the new location of the treatment volume 24. Since the above measurements and feedback signals are performed at electronic speeds and the cardiac cycle is relatively slow in comparison, it is possible for the refocused beam 22 to remain on target with the movement of the treatment volume 24 throughout the cardiac cycle.

As generally outlined, non-invasive ultrasound imaging techniques can be employed to determine the "moved" position of the treatment volume 24 relative to the known position of the refocused beam 22.

Aberration correction and motion compensation can be achieved through implementation of variously known algorithms in the relevant technical field, as will be appreciated by one skilled in this technological field. For example, aberration compensation and movement correction can be generally accomplished by the following procedure: measuring the magnitude and phase of the acoustic pressure at each focal point produced by each individual transducer 20 of the array after encountering an aberration or movement; calculating a full rank matrix based on the acoustic pressure measurement to include phase errors due to the aberrations and movement; setting a weighing matrix as an identity matrix and specifying the required intensity distribution at the focal points; calculating the driving signal for one transducer 20 based on the measured data; and repeating the above for each additional transducer 20.

Actual driving of the array 16 is performed by the controller 12 and the drivers 14, while refocusing and motion tracking is assisted through the phase detection system 18. Generally, these components can be referred to as the phased array driving portion of the system 10. Electronically, the former components can be seen as including three major subsystems; a digital subsystem, an analogue subsystem and a power supply subsystem.

The digital subsystem consists of the controller 12, which includes a 486 DX computer 51, an interface board 52, buffer boards 54 and FIFO boards 56 that cooperate to generate up to 512 channels of square waves with specified phases and amplitudes per duty cycles. While only 512 channels are implemented in the following discussion, it will be understood that additional channels are possible. Each channel is amplified and matched in the analog subsystem to the impedance of the corresponding transducer 20 which will be driven by that channel.

The interface board 52 is a 4.8 inch by 6.5 inch custom printed circuit (PC) board that is plugged in the appropriate slot of the controller 12. This board 52 serves as an interface between the computer 51 and the buffer boards 54 and FIFO boards 56 which are located in a card cage 58.

Figure 4:
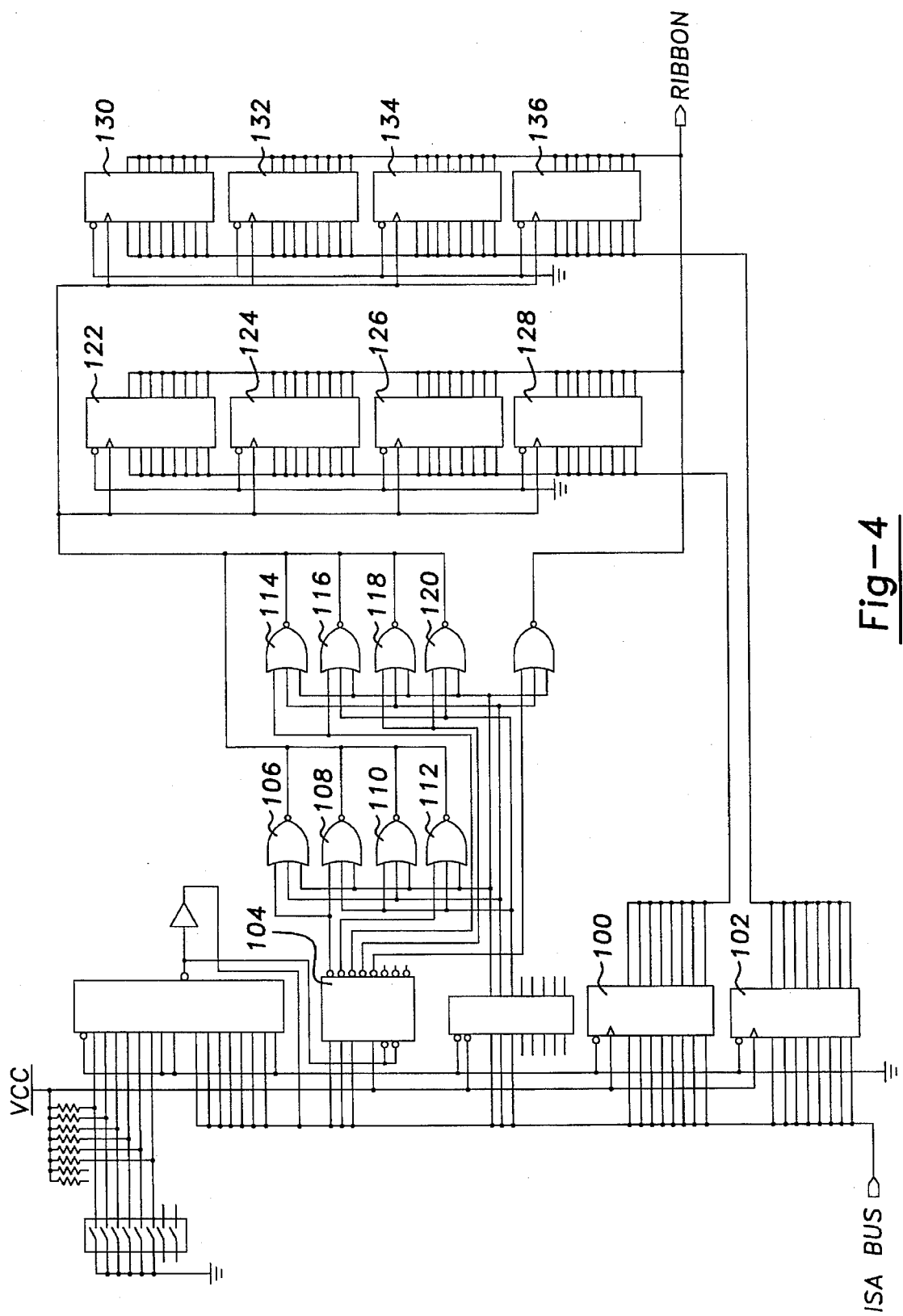
FIG. 4 is a circuit diagram of the interface boards used in the present invention.

As seen in FIG. 4, on the interface board 52, two latches, 100 and 102, latch the I/O data bus from the computer. One of eight decoders, 104, inputs three address lines, A1–A3, and decodes eight outputs to select eight 3-input NOR gates 106, 108, 110, 112, 114, 116, 118 and 120. The outputs of the NOR gates connect to the chip_select inputs of eight output latches 122, 124, 126, 128, 130, 132, 134, 136, four of which 122, 124, 126, 128 are used to latch the 32-bit data bus, D0–D31, three 130, 132, 134 to a latch the 24-bit address bus, A0–A23, (only part of them are use in this system) and one 136 to latch 8-bit control bus comprising: OE_, RS_, REN_, WEN_, CLKEN_, CLKSEL_, PLSCTRL_, FBCTRL_, where:

| | |
|---|---|
| OE_: | output_enable line for the Parallel SyncFIFOs |
| RS_: | reset line for the Parallel SyncFIFOs |
| REN_: | read_enable line for the Parallel SyncFIFOs |
| WEN_: | write_enable line for the Parallel SyncFIFOs |
| CLKEN_: | the input of the D flip-flop, 152, on the buffer boards |
| CLKSEL: | clock select: to select between two kinds of clock signals for the Parallel SyncFIFOs. When high, the clock for the Parallel SyncFIFOs is low frequency and data is written into the Parallel SyncFIFOs. When low, the clock for the Parallel SyncFIFOs is high frequency and the Parallel SyncFIFOs output data. |
| PLSCTRL_: | pulse_control line: When low, the outputs of the Parallel SyncFIFO boards are enabled in tri-state. When high, the outputs of the Parallel SyncFIFO boards are enabled in tri-state. |
| FBCTRL_: | feedback_control line: When low, the output of the Parallel SyncFIFOs is feedback to input. |

Figure 5:
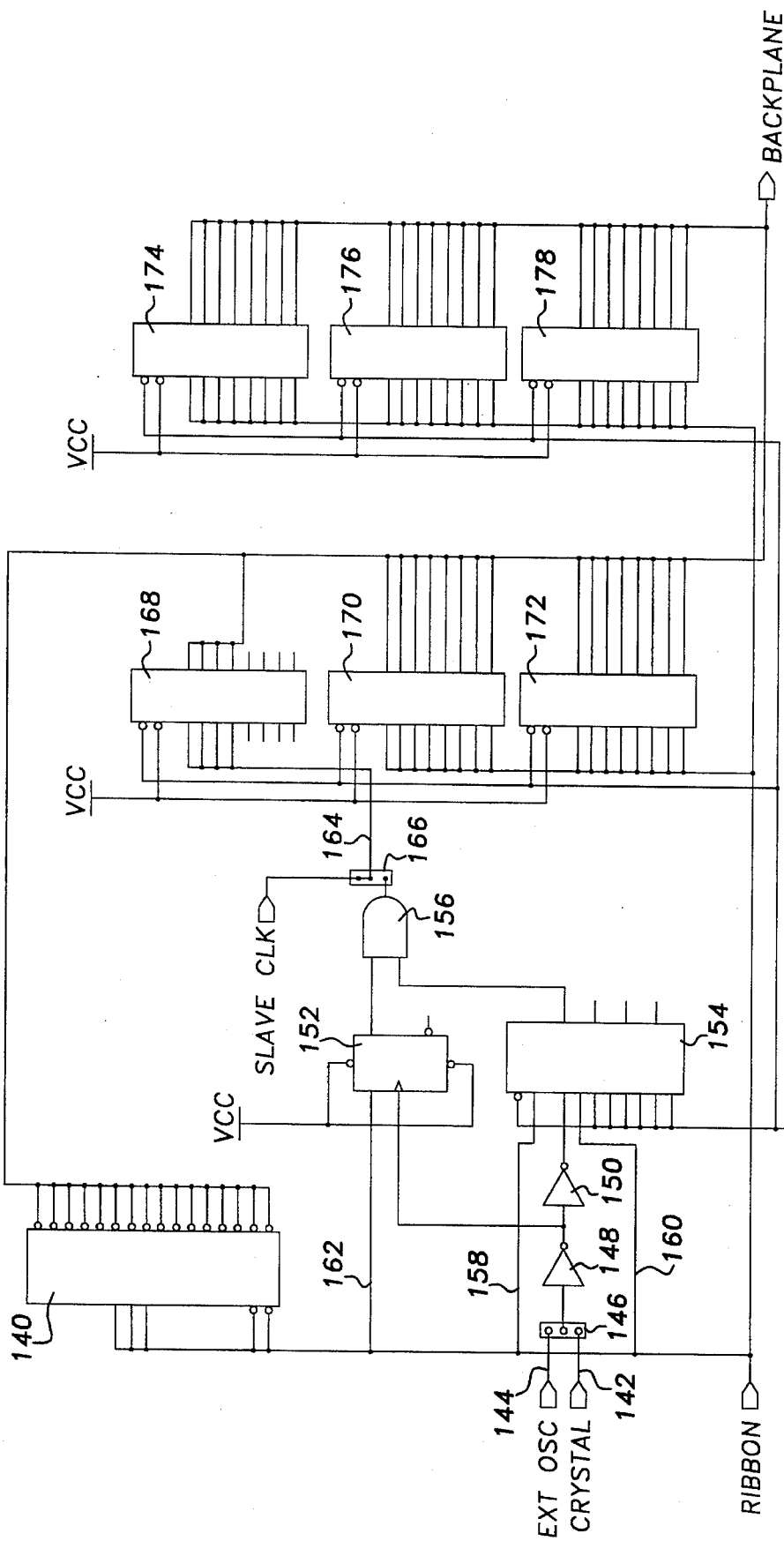
FIG. 5 is a circuit diagram of the buffer boards used in the present invention.

The buffer boards 54, a representative one of which is shown in FIG. 5, buffer the data bus, the clock and the control bus going to the FIFO boards 56. Each buffer board 54 can drive up to eight FIFO boards 56. But in the present system, for design convenience, one buffer board 54 is used to drive two FIFO boards 56.

One decoder of sixteen, 140, inputs four address lines, A1–A4, and outputs a 16-bit BOARD_ENABLE bus. Each output enables one FIFO board 56 when writing data into the Parallel SyncFIFOs. Address lines A4 and A5 are used to chip_select the decoder 140.

The buffer boards 54 also generate and buffer the clock. The original clock source can be provided in two ways. One is to use a crystal oscillator 142 on the board 54 and the other way is to input an external clock signal 144 from a signal generator. A switch, 146, on board 54 allows the user to select either. The clock generation circuit is made up of two inverters, 148 and 150, one D flip-flop, 152, one 2-input multiplexer, 154 and one AND gate, 156. Two kinds of clock signals need to be generated. The first is a lower frequency clock signal used when writing the data into the Parallel SyncFIFOs. In this case, the CLKSEL 158 is high (1) and the output of the multiplexer 154 is the same as the STROBE signal 160. When the CLKEN_ signal is enabled (low 0), the output of the clock generation circuit 164 is equal to the STROBE signal 160, i.e. low frequency clock. The other clock signal is a high frequency clock used when the Parallel SyncFIFOs are outputting the data. In this case, the CLKSEL 158 is low (0) and output of multiplexer 154 is the same as original clock source, either the external source 144 or the internal source 142. When the CLKEN_ signal 162 is enabled (low, 0), the output of the clock generation circuit 164 is equal to the original clock source, i.e. high frequency clock. In either case, as long as the CLKEN_ signal 162 is disabled (high, 1), the output of the clock generation circuit 164 is low (0).

To assure the same clock signal controlling all FIFO boards 56, there should be only one clock source from a master buffer board 54 (either internal or external). All the other buffer boards 54 (slave buffer boards) receive the clock signal from the master board 54. A switch 166 on each buffer board allows the user to specify the board as a master or slave board.

Six 8-bit buffers 168, 170, 172, 174, 176 and 178 are provided on the buffer board 54. One, 168, buffers the clock signal exclusively while the others, 172, 174, 176 and 178, buffer the 32-bit data bus and one, 170, buffers the modified control bus, OE_, RS_, REN_, WEN_, A6, A7, FBC-TRL_ and PLSCTRL_. A6 and A7 originate from the address bus and are used as control lines for the FIFO boards 56.

The FIFO boards 56 are generally responsible for waveform generation and each board is constructed to generate 32 channels of square wave with specified phases and magnitudes (duty cycles). Each channel, after being amplified and matched to the impedance of its corresponding array transducer 20, will drive that particular transducer 20 of the array 16. The specified phase and magnitude data are stored in the Parallel SyncFIFOs and each square wave is generated by repeatedly reading this data from the Parallel SyncFIFOs.

Figure 6:
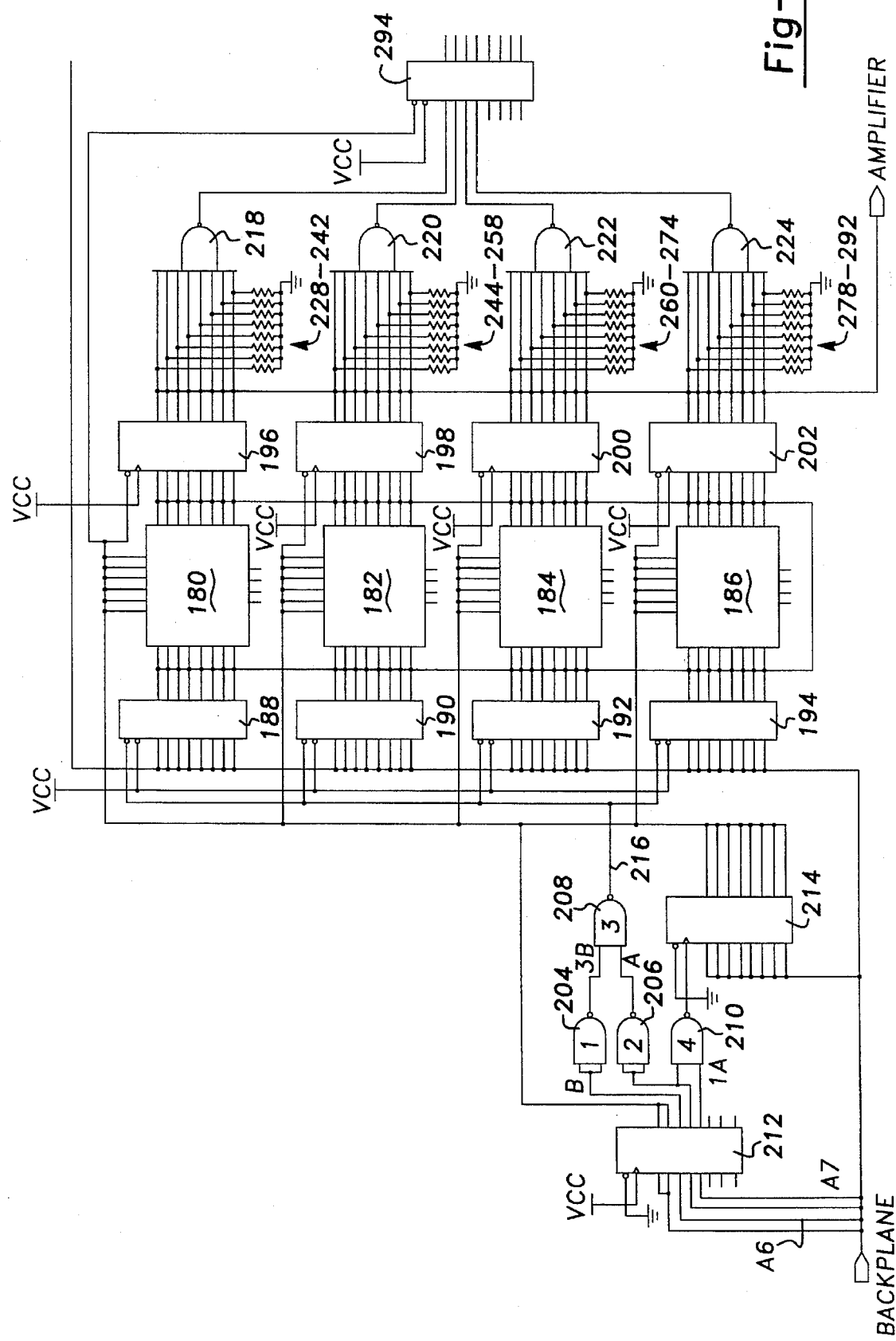
FIG. 6 is a circuit diagram of the FIFO boards used in the present invention.

Referring now to FIG. 6, each FIFO board 56 consists of four 512×8-bit Parallel SyncFIFOs, 180, 182, 184 and 186, with four 8-bit input buffers, 188, 190, 192 and 194 and four 8-bit output latches, 196, 198, 200 and 202, some control logic and some feedback logic.

The control logic is made up of four 2-input NAND gates, 204, 206, 208 and 210, and two 8-bit latches, 212 and 214. A6, mentioned above, serves as a control line to control the output_enable of the four 8-bit input buffers, 188, 190, 192 and 194, i.e. when A6 is high (1) and the BOARD_ENABLE line 216 is enabled (low, 0), the output_enables of the four input buffers 188, 190, 192 and 194 are activated (low, 0) so that data can flow into the buffers. When A6 is low (0), the output_enable of the four input buffers 188, 190, 192 and 194 are inactivated and data cannot flow into the buffers. A7, mentioned above, serves as an all channel control line. This is used when finishing writing data into all the Parallel SyncFIFOs 180, 182, 184 and 186 and all the Parallel SyncFIFOs 180, 182, 184 and 186 need to start outputting data at the same time. When writing data into a particular board, its BOARD_ENABLE line 216 is activated (low, 0) and A7 has no effect regardless of its status. When all Parallel SyncFIFOs 180, 182, 184 and 186 start outputting data at the same time, all the BOARD_ENABLE lines 216 are inactivated (high, 1) and A7 is low (0) so that the control bus latch 212 on each FIFO board 56 is selected and all the Parallel SyncFIFOs 180, 182, 184 and 186 are acting the same.

The core of each FIFO board 56 includes the four 512× 8-bit Parallel SyncFIFOs, 180, 182, 184 and 186; the four 8-bit input buffers, 188, 190, 192 and 194; and the four 8-bit output latches 196, 198, 200 and 202, which cooperate to generate 32 channels of square waves, simultaneously. The input buffers 188, 190, 192 and 194 buffer the data prior to the Parallel SyncFIFOs 180, 182, 184 and 186 and output latches 196, 198, 200 and 202 latch the output data from the Parallel SyncFIFOs 180, 182, 184 and 186. Each output bit of a Parallel SyncFIFO makes one channel of square wave and every FL words makes a complete waveform ($\log_2$FL-bit resolution), where the number FL (FIFO Length), is related to the frequency of the square waves by the following formula:

$$\text{freq. of square wave} = 48\text{MHz/FL} \qquad (1)$$

where 48 MHz is the frequency of the original clock source from the buffer board 54.

Accordingly, the frequency of the square waves can be changed by either changing the frequency of the original clock source or the number FL. It should be noted that the number FL should not be less than 32 in order to guarantee no less than 5-bit resolution and should not be greater than 512, which is the total depth of the FIFO boards. The value of number FL is specified so that, using 48 MHz as the original clock source, the frequency range of the square waves generated is 93.75 KHz to 1.5 MHz. The square waves are generated as follows. First, write one complete waveform with specified phases and amplitudes into the four Parallel SyncFIFO 180, 182, 184 and 186 on board #0, i.e. FL words. At this moment, the write_pointer of the each Parallel SyncFIFO is located FL while the read_pointer remains at location 0. Second, do the same procedure for all the other boards until the Parallel SyncFIFOs on each FIFO board 56 is written in one complete waveform. Third, start all channel control action (all BOARD_ENABLE lines 214 high, A7 low) and let all FIFOs 56 start synchronous reading and writing so the FIFOs 56 repeat reading and writing the same waveform data and output continuous square waves.

Feedback logic is used as a self-test circuit for FIFO boards 56. Prior to using the FIFO boards, data is written into the Parallel SyncFIFOs 180, 182, 184 and 186 and, by checking the internal feedback signals, we can tell if the FIFO boards 56 are properly functioning. The feedback logic includes four 8-input NAND gates, 218, 220, 222, 224, 32 pull-up resistors 228 through 292 and one feedback buffer, 294. Each NAND gate inputs, through nine corresponding output latches, the outputs of each Parallel SyncFIFO to the feedback buffer 294. By initially writing all 1's into the Parallel SyncFIFOs 180, 182, 184 and 186, if the feedback signals are 0, it means that the FIFO boards 56 are working properly.

The digital subsystem needs only a +5 v power supply 58. The output square wave has a magnitude (note: this is different from the duty cycle) of 5 v and a wide frequency range.

The analog subsystem contains the amplifier boards 60 and the matching boards 62, which respectively amplify the square waves generated by the digital subsystem and match them to the impedance of the array's individual transducers 20.

Figure 7:
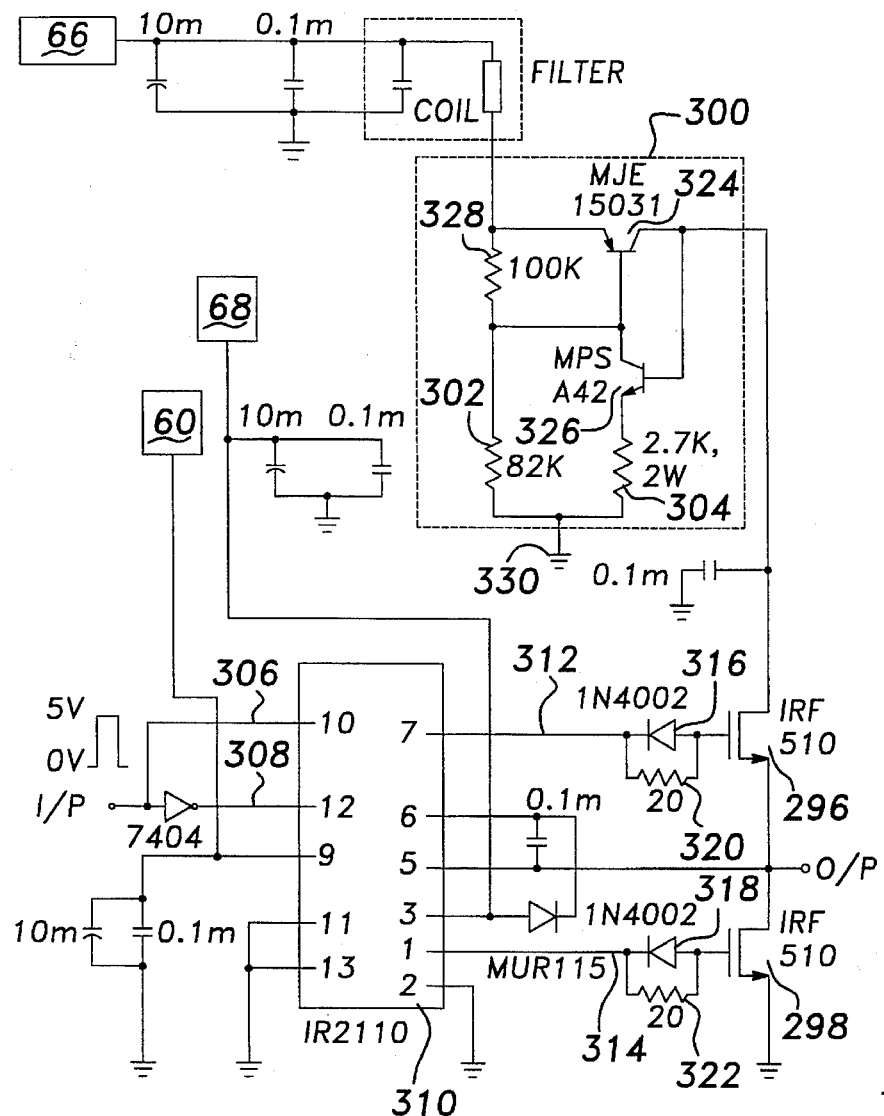
FIG. 7 is a circuit diagram of the amplifier circuit used in the present invention.

Each amplifier board 62, as seen in FIG. 7, contains the power drivers 296 and 298, as well as shod circuit protection circuit 300, and each board drives sixteen channels of the array 16. The output of the boards 62 is driven by a pair of N-channel MOSFETs IRF510 transistors 296 and 298. In case a short circuit occurs (on or beyond the amplifier output), a short circuit protection circuit 300 cuts the main DC supply 66 current (to the corresponding pair of channels) to a low (i.e. safe) level. There are eight of these protection circuits for the sixteen channels. Also, an LEDs on the backplane board can be provided to light up, indicating a short circuit presence on the corresponding amplifier board's output.

Depending on the maximum supply voltage that the circuit will have to work under, two resistors are 302 and 304 accordingly provided. The maximum voltage must be established such that a amplifier board 62 will supply 10 watts (or less) per transducer 20 (on average) at the maximum voltage per the table below:

| Max. volt. | R1 (302) | Rp (304) |
|---|---|---|
| 40 | 82 K | 2.7 K, 3 W |
| 50 | 120 K | 3.3 K, 3 W |
| 60 | 270 K | 4 K, 3 W |
| 70 | 680 K | 5.6 K, 3 W |

The circuitry of the amplifier boards 62 converts the Transistor-Transistor Logic (TTL) level digital control signal to a level which is high enough to drive the piezoelectric transducers 20 of the array 16. Two opposite TTL signals 306 and 308 are the inputs to the MOSFET driver 310, which converts the signals into two opposite CMOS level (0–15 v) signals 313 and 314. These signals drive the gates of the two MOSFET power transistors 296 and 298 that compose the output stage of the amplifier circuit as a class E amplifier.

In the class E amplifier, the two transistors 296 and 298 should not be allowed to be ON simultaneously. If both transistors are ON, an effective short circuit occurs between the DC power supply 66 and the ground, with only fractions of 1Ω (transistors drain-source on-state resistors) in the way. This short circuit lowers the efficiency of the amplifier and heats up the transistors 296 and 298.

To prevent the simultaneous conduction, beside the fact that the inverted TTL signal 308 suffers some delay compared to the non-inverted one 306, two other measures are taken. First, the MOSFET drivers have a turn on delay that is 25 ns. longer than the turn off delay. The transistors turn off delay is <25 ns. Second, each gate of the transistors are driven through a parallel circuit of a diode 316 and 318 and a 20Ω resistor 320 and 322. Accordingly, this circuit provides a one-way delay. The resistors 320 and 322 increase the RC time constant of the corresponding transistor gate, this causes some delay in the turn-on time, but does not effect the turn-off time due to the negligible forward resistance of the diodes 316 and 318. Heat sinks are used with the transistors 296 and 298 to help dissipating any excessive heat.

Short circuit protection in the amplifier boards 60 consist of a power p-n-p transistor 324 a small signal n-p-n transistor 326 and three resistors 302, 304 and 328. The p-n-p transistor 324 limits the main DC supply 66 current, which is always ON under normal running conditions. The base current of the p-n-p transistor 324 is sunk through the collector of the n-p-n transistor 326. When a short circuit occurs on or beyond the amplifier output, the p-n-p transistor 324 turns OFF, because the n-p-n transistor 326 cannot sink the required base current of the p-n-p transistor 324. This current is controlled by power (Rp) resistor 304 between the emitter of the n-p-n transistor 326 and the ground 330. When a short circuit happens, a corresponding red light-emitting diode on the back panel board lights up.

Figure 8:
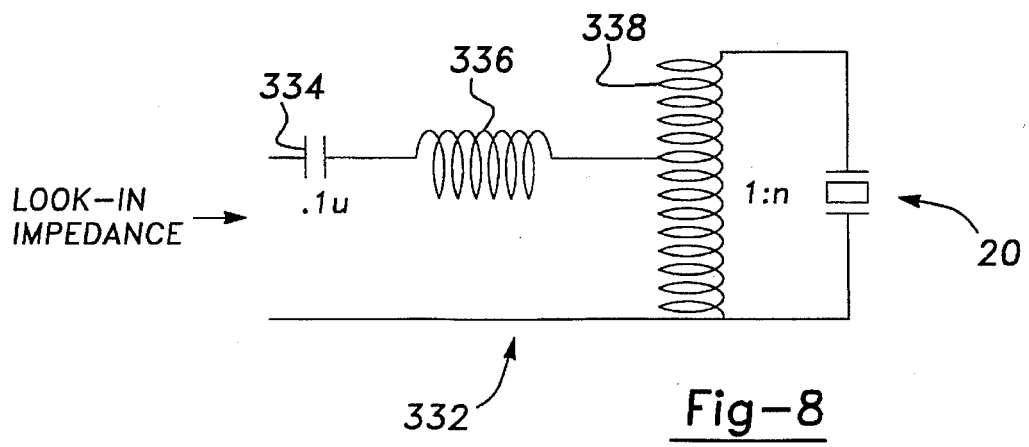
FIG. 8 is a circuit diagram of the matching circuits utilized in FIG. 3.

Matching boards 64 are coupled between the amplifier boards 62 and the array 16. The matching boards 64 are used to match the impedance of the transducers 20 with their respective square wave signals. Since the impedance of transducers 20 has capacitance part, the matching boards 64 are designated to have inductance part. This is so that the overall impedance of the load to amplifiers tends to pure resistance. Each matching board 64 has sixteen channels and the basic circuit 70 for each channel is as shown in FIG. 8.

The circuit 332 is made up of a 0.1μ, 100 V capacitor 334, a custom-wound inductor 336 and a custom-wound transformer 338. The primary-to-secondary ratio of the transformer 338 is decided according to the impedance of the transducers 20. Once the transformer 338 has been chosen, user can adjust the turns of the indicator to make best match. In the presently described system, the ratio of the transformers was 1:2 to 1:4.

While the above description constitutes the preferred embodiment of the present invention, it will be appreciated that the invention is susceptible to modification, variation and change without departing from the proper scope and fair meaning of the accompanying claims.

We claim:

1. An ultrasound system for performing cardiac ablation on a patient, said ultrasound system comprising:

an array adapted for external positioning relative to the body of the patient, said array including a plurality of ultrasound transducers capable of producing ultrasonic energy in the form of a focused ultrasound beam, said beam being of sufficient energy to ablate a predetermined cardiac tissue volume of the patient;

control means for producing phased electrical control signals controlling production of phased ultrasound waves by individual ones of said transducers, said ultrasound waves cooperating to form said beam;

drive means coupled to said control means and said transducers for driving said transducers, said drive means amplifying said control signals and producing individual channels of phased electrical current, said electrical current being applied to individual ones of said transducers in accordance to said control signals; and focus correcting means for refocusing said beam after defocusing by acoustical aberrations resulting from inhomogeneous tissue between said array and the predetermined cardiac tissue volume, said focus correcting means including sensor means for sensing said waves produced by said transducers after said waves have encountered said aberrations, said sensor means being coupled to said control means and providing feedback signals thereto indicative of said aberrations, whereby said control means determines and communicates compensating control signals to said drive means which accordingly drive said transducers in response thereto so as to produce and form a refocused beam on said predetermined cardiac tissue volume thereby compensating for said acoustical aberrations and enabling cardiac ablation to be performed.

2. An ultrasound system as set forth in claim 1 wherein said focus correcting means includes a catheter and at least one sensor supported thereon, said catheter having a proximal end and a distal end with said distal end being adapted for insertion within the heart of the patient generally adjacent to said predetermined cardiac tissue volume.

3. An ultrasound system as set forth in claim 2 wherein said sensor is adapted to sense a phase distribution of said waves after encountering said acoustical aberrations, said sensor also being coupled to said control means to provide aberration feedback signals indicative of said phase distribution of said defocused beam.

4. An ultrasound system as set forth in claim 3 wherein said control means is adapted to receive said aberration feedback signals, determine a compensating driving phase distribution and produce compensating control signals communicated to said drive means, said drive means subsequently driving said transducers according to said compensating control signals so as to produce ultrasound waves compensating for said aberrations and forming said refocused beam on said predetermined cardiac tissue volume.

5. An ultrasound system as set forth in claim 2 wherein said focus correcting means includes a plurality of sensors.

6. An ultrasound system as set forth in claim 2 wherein said sensor is a hydrophone sensor.

7. An ultrasound system as set forth in claim 1 wherein said focus correcting means includes a portion adapted to be inserted within the patient and said system is relatively non-invasive.

8. An ultrasound system as set forth in claim 1 wherein said focus correcting means is adapted to be located externally of the patient and said system is wholly non-invasive.

9. An ultrasound system as set forth in claim 8 wherein said focus correcting means includes an ultrasound sensing means for sensing reflected portion of said beam caused by said acoustical aberrations.

10. An ultrasound system as set forth in claim 8 wherein said focus correcting means includes ultrasound sensing means for sensing said beam after said beam encounters said acoustical aberrations.

11. An ultrasound apparatus for performing non-invasive cardiac ablation on a patient, said ultrasound apparatus comprising:

an array adapted for positioning relative to the body of the patient, said array including a plurality of ultrasound transducers capable of producing ultrasonic energy in the form of a focused ultrasound beam, said beam being of sufficient energy to ablate a predetermined cardiac tissue volume of the patient;

control means for producing phased electrical control signals controlling production of phased ultrasound waves by individual ones of said transducers, said ultrasound waves cooperating to form said beam;

drive means coupled to said control means and said transducers for driving said transducers, said drive means amplifying said control signals and producing individual channels of phased electrical current, said electrical current being applied to individual ones of said transducers in accordance to said control signals; and focus correcting means for refocusing said beam after defocusing by acoustical aberrations resulting from inhomogeneous tissue between said array and the predetermined cardiac tissue volume, said focus correcting means including sensor means for sensing said waves produced by said transducers after said waves have encountered said aberrations, said sensor means being coupled to said control means and providing feedback signals thereto indicative of said aberrations, whereby said control means determines and communicates compensating control signals to said drive means which accordingly drive said transducers in response thereto so as to produce and form a refocused beam on said predetermined cardiac tissue volume thereby compensating for said acoustical aberrations and enabling cardiac ablation to be performed, said focus correcting means also for refocusing said beam on said predetermined cardiac tissue volume after movement of said predetermined cardiac tissue volume whereby said beam follows movement of said predetermined cardiac tissue volume while performing ablation.

12. An ultrasound system as set forth in claim 11 wherein said focus correcting means includes a catheter and at least one sensor supported thereon, said catheter having a proximal end and a distal end with said distal end being adapted for insertion within the heart of the patient generally adjacent to said predetermined cardiac tissue volume.

13. An ultrasound system as set forth in claim 12 wherein said sensor is adapted to sense a phase distribution of said waves after encountering said acoustical aberrations, said sensor being coupled to said control means to provide aberration feedback signals indicative of said phase distribution of said defocused beam, said control means utilizing said aberration feedback signals to determine a compensating driving phase distribution and produce compensating control signals communicated to said drive means, said drive means subsequently driving said transducers according to said compensating control signals so as to produce ultrasound waves compensating for said aberrations and forming said refocused beam on said predetermined cardiac tissue volume.

14. An ultrasound system as set forth in claim 12 wherein said focus correcting means includes a hydrophone array.

15. An ultrasound system as set forth in claim 11 wherein said focus correcting means includes a portion adapted for insertion within the patient, said system being relatively non-invasive.

16. An ultrasound system as set forth in claim 11 wherein said focus correcting means includes ultrasound sensing means for sensing said beam after said beam encounters said acoustical aberrations.

17. An ultrasound system as set forth in claim 11 wherein said focus correcting means is adapted to be located externally of the patient, said system being wholly non-invasive.

18. An ultrasound system as set forth in claim 17 wherein said focus correcting means includes an ultrasound sensing means for sensing reflected portion of said beam caused by said acoustical aberrations.

19. A method for performing ablation of a predetermined cardiac tissue volume of a patient utilizing ultrasound energy, said method comprising the steps of:

providing an ultrasound array capable of producing a focused beam of ultrasonic energy;

providing a controller for controlling focusing of said beam;

locating said array externally of the patient;

mapping cardiac tissue to determine a treatment volume, said treatment volume including cardiac tissue responsible for the occurrence of arrhythmia;

focusing said beam on said treatment volume after determination thereof;

sensing an initial phase distribution of said beam, said initial phase distribution being unfocused as a result of acoustic aberrations caused by inhomogeneous tissues of the patient;

providing feedback signals to said controller, said signals corresponding to said initial phase distribution;

determining a compensating phase distribution based on said signals, said compensating phase distribution compensating for said acoustical aberrations and being determined by said controller;

refocusing said beam on said treatment volume while compensating for said acoustical aberrations; and ablating said treatment volume after refocusing said beam thereon.

20. The method set forth in claim 19 further comprising the step of mapping said cardiac tissue through a non-invasive procedure.

21. The method set forth in claim 20 wherein said procedure includes ultrasound imaging.

22. The method set forth in claim 19 further comprising the step of mapping said cardiac tissue through an invasive procedure.

23. The method set forth in claim 22 wherein said procedure includes utilizing a catheter based probe.

24. The method set forth in claim 23 wherein said catheter based probe is a hydrophone array.

25. The method set forth in claim 19 further comprising the step of sensing said initial phase distribution through a non-invasive procedure.

26. The method set forth in claim 25 wherein said procedure includes ultrasound imaging.

27. The method set forth in claim 19 further comprising the step of sensing said initial phase distribution through an invasive procedure.

28. The method set forth in claim 27 wherein said invasive procedure includes a catheter based probe.

29. The method set forth in claim 27 wherein said invasive procedure includes a hydrophone array.

30. The method set forth in claim 19 further comprising the step of tracking movement of said treatment volume and refocusing said beam so as to follow said movement of said treatment volume while performing ablation.

31. The method set forth in claim 30 wherein said step of tracking movement of said treatment volume is performed through a non-invasive procedure.

32. The method set forth in claim 31 wherein said procedure involves ultrasound imaging.

33. The method set forth in claim 30 wherein said step of tracking movement of said treatment volume is performed through an invasive procedure.

34. The method set forth in claim 33 wherein said invasive procedure utilizes a catheter based probe.

35. The method set forth in claim 34 wherein said probe is a hydrophone array.

36. The method set forth in claim 19 wherein said compensating phase distribution is based upon ultrasound waves transmitted through inhomogeneous tissue of the patient.

37. The method set forth in claim 19 wherein said compensating phase distribution is based upon ultrasound waves reflected from said patient.

38. The method set forth in claim 19 wherein said refocusing step is performed multiple times during one cardiac cycle.

39. The method set forth in claim 30 wherein said tracking step is performed multiple times during one cardiac cycle.

* * * * *